United States Patent [19]
Rains

[11] Patent Number: 5,775,340
[45] Date of Patent: Jul. 7, 1998

[54] LONG HANDLE TOENAIL CLIPPERS

[76] Inventor: David Rains, 1842-A Williams Rd., Monroe, N.C. 28110

[21] Appl. No.: 906,117

[22] Filed: Jul. 25, 1997

[51] Int. Cl.$^6$ .................................................. A45D 29/02
[52] U.S. Cl. .................... 132/73.5; 30/28; 132/75.5
[58] Field of Search .................... 132/75.4, 75.5, 132/73.5; 30/26, 27, 28, 29

[56] References Cited

U.S. PATENT DOCUMENTS

| | | | |
|---|---|---|---|
| 527,240 | 10/1894 | Garies | 30/28 |
| 766,859 | 8/1904 | Wilcox | 132/75.5 |
| 857,790 | 6/1907 | Carroll | 132/75.5 |
| 4,847,994 | 7/1989 | Dunn, Jr. | 132/73 |
| 4,893,406 | 1/1990 | Larson | 30/28 |
| 5,357,677 | 10/1994 | West | 132/73.5 |
| 5,546,658 | 8/1996 | MacLeod et al. | 30/28 |

*Primary Examiner*—Todd E. Manahan

[57] ABSTRACT

A new Long Handle Toenail Clipper for allowing a person to cut their toenail without needed to bend over. The inventive device includes a conventional nail clipper having a cutting portion and an actuating lever. A triangular base is positioned below and is secured to a lower segment of the cutting portion. The triangular base orients the nail clipper with a forward end of the nail clipper disposed below a rearward end of the nail clipper. A telescopic handle is coupled to the actuating lever of the nail clipper.

7 Claims, 2 Drawing Sheets

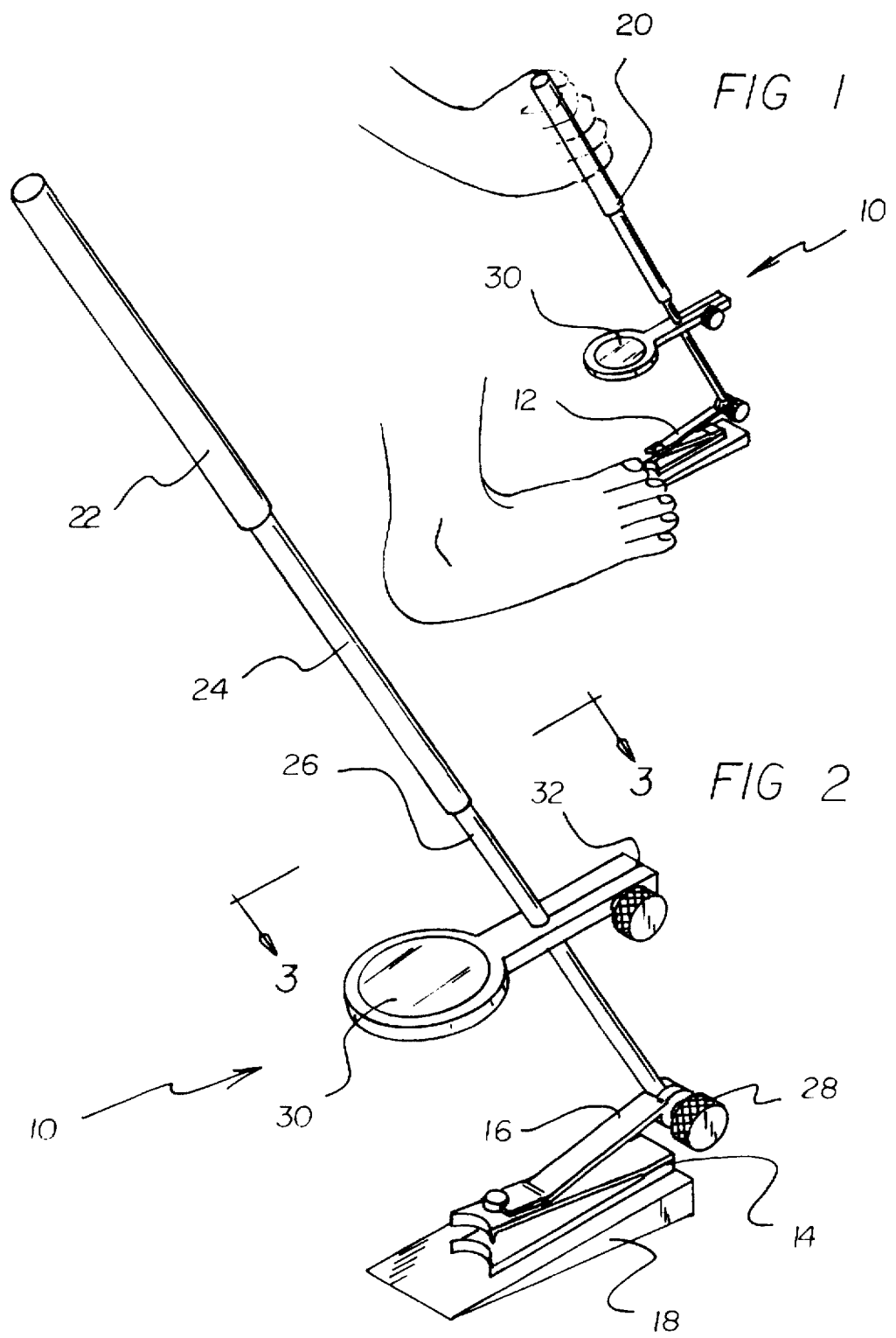

LONG HANDLE TOENAIL CLIPPERS

BACKGROUND OF THE INVENTION

1. Field of the Invention

The present invention relates to TOE NAIL CLIPPERS and more particularly pertains to a new Long Handle Toenail Clippers for ALLOWING A PERSON TO CUT THEIR TOENAILS WITHOUT NEEDING TO BEND OVER.

2. Description of the Prior Art

The use of TOE NAIL CLIPPERS is known in the prior art. More specifically, TOE NAIL CLIPPERS heretofore devised and utilized are known to consist basically of familiar, expected and obvious structural configurations, notwithstanding the myriad of designs encompassed by the crowded prior art which have been developed for the fulfillment of countless objectives and requirements.

Known prior art TOE NAIL CLIPPERS include U.S. Pat. No. 4,893,406 to Larson; U.S. Pat. No. 5,357,677 to West; U.S. Pat. No. Des. 329,306 to Rommerdale; U.S. Pat. No. 4,176,449 to Lee et al.; U.S. Pat. No. 4,564,034 to Mackel; and U.S. Pat. No. 4,847,994 to Dunn, Jr.

While these devices fulfill their respective, particular objectives and requirements, the aforementioned patents do not disclose a new Long Handle Toenail Clippers. The inventive device includes a conventional nail clipper having a cutting portion and an actuating lever. A triangular base is positioned below and is secured to a lower segment of the cutting portion. The triangular base orients the nail clipper with a forward end of the nail clipper disposed below a rearward end of the nail clipper. A telescopic handle is coupled to the actuating lever of the nail clipper.

In these respects, the Long Handle Toenail Clippers according to the present invention substantially departs from the conventional concepts and designs of the prior art, and in so doing provides an apparatus primarily developed for the purpose of ALLOWING A PERSON TO CUT THEIR TOENAILS WITHOUT NEEDING TO BEND OVER.

SUMMARY OF THE INVENTION

In view of the foregoing disadvantages inherent in the known types of TOE NAIL CLIPPERS now present in the prior art, the present invention provides a new Long Handle Toenail Clippers construction wherein the same can be utilized for ALLOWING A PERSON TO CUT THEIR TOENAILS WITHOUT NEEDING TO BEND OVER.

The general purpose of the present invention, which will be described subsequently in greater detail, is to provide a new Long Handle Toenail Clippers apparatus and method which has many of the advantages of the TOE NAIL CLIPPERS mentioned heretofore and many novel features that result in a new Long Handle Toenail Clippers which is not anticipated, rendered obvious, suggested, or even implied by any of the prior art TOE NAIL CLIPPERS, either alone or in any combination thereof.

To attain this, the present invention generally comprises a conventional nail clipper having a cutting portion and an actuating lever. A triangular base is positioned below and securing to a lower segment of the cutting portion. The triangular base orients the nail clipper with a forward end of the nail clipper disposed below a rearward end of the nail clipper. A telescopic handle is coupled to the actuating lever of the nail clipper. The telescopic handle has an upper portion, an intermediate portion and a lower portion. The lower portion is pivotally coupled with the actuating lever of the nail clipper. A locking knob extends through the lower portion and the actuating lever for selectively locking the lower portion with respect to the actuating lever to preclude pivotal rotation. A magnifying lens is coupled with respect to the lower portion of the telescopic handle disposed above the nail clipper. The magnifying lens has a bifurcated outer end portion slidably receiving the lower portion of the telescopic handle therein. A locking knob extends through the bifurcated outer end portion for selectively locking the magnifying lens with respect to the lower portion to preclude sliding of the lens.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Long Handle Toenail Clippers apparatus and method which has many of the advantages of the TOE NAIL CLIPPERS mentioned heretofore and many novel features that result in a new Long Handle Toenail Clippers which is not anticipated, rendered obvious, suggested, or even implied by any of the prior art TOE NAIL CLIPPERS, either alone or in any combination thereof.

It is another object of the present invention to provide a new Long Handle Toenail Clippers which may be easily and efficiently manufactured and marketed.

It is a further object of the present invention to provide a new Long Handle Toenail Clippers which is of a durable and reliable construction.

An even further object of the present invention is to provide a new Long Handle Toenail Clippers which is susceptible of a low cost of manufacture with regard to both materials and labor, and which accordingly is then susceptible of low prices of sale to the consuming public, thereby making such Long Handle Toenail Clippers economically available to the buying public.

Still yet another object of the present invention is to provide a new Long Handle Toenail Clippers which provides in the apparatuses and methods of the prior art some of the advantages thereof, while simultaneously overcoming some of the disadvantages normally associated therewith.

Still another object of the present invention is to provide a new Long Handle Toenail Clippers for ALLOWING A PERSON TO CUT THEIR TOENAILS WITHOUT NEEDING TO BEND OVER.

Yet another object of the present invention is to provide a new Long Handle Toenail Clippers which includes a conventional nail clipper having a cutting portion and an actuating lever. A triangular base is positioned below and is secured to a lower segment of the cutting portion. The triangular base orients the nail clipper with a forward end of the nail clipper disposed below a rearward end of the nail clipper. A telescopic handle is coupled to the actuating lever of the nail clipper.

Still yet another object of the present invention is to provide a new Long Handle Toenail Clippers that can be designed with a magnifying glass to aid persons whose vision is impaired.

Even still another object of the present invention is to provide a new Long Handle Toenail Clippers that will aid the oversized, the elderly and the physically challenged.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new Long Handle Toenail Clippers according to the present invention illustrated in use.

FIG. 2 is a perspective view of the present invention.

DESCRIPTION OF THE PREFERRED EMBODIMENT

Figure 3:
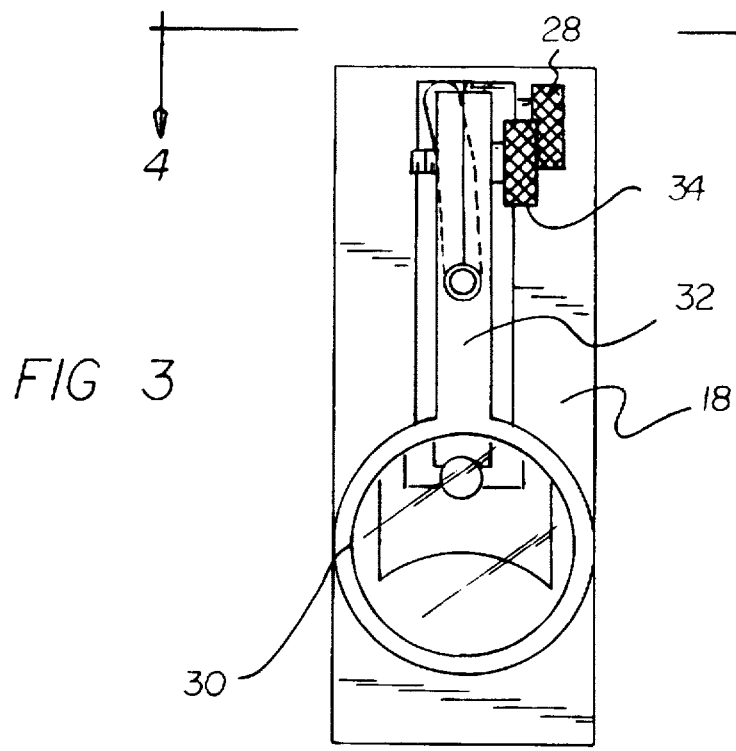
FIG. 3 is a cross-sectional view of the present invention as taken along line 3—3 of FIG. 2.
Figure 4:
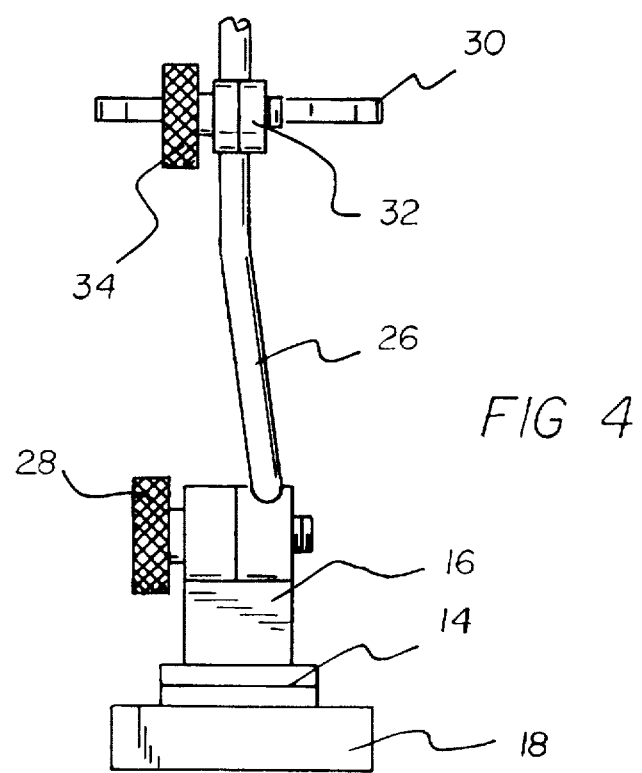
FIG. 4 is a rear elevation view of the present invention as taken along line 4—4 of FIG. 3.

With reference now to the drawings, and in particular to FIGS. 1 through 4 thereof, a new Long Handle Toenail Clippers embodying the principles and concepts of the present invention and generally designated by the reference numeral 10 will be described.

As best illustrated in FIGS. 1 through 4, the Long Handle Toenail Clippers 10 comprises a conventional nail clipper 12 having a cutting portion 14 and an actuating lever 16.

A triangular base 18 is positioned below and is secured to a lower segment of the cutting portion 14. The triangular base 18 orients the nail clipper 12 with a forward end of the nail clipper 12 disposed below a rearward end of the nail clipper 12.

A telescopic handle 20 is coupled to the actuating lever 16 of the nail clipper 12. The telescopic handle 20 has an upper portion 22, an intermediate portion 24 and a lower portion 26. The lower portion 26 is pivotally coupled with the actuating lever 16 of the nail clipper 12. A locking knob 28 extends through the lower portion 26 and the actuating lever 16 for selectively locking the lower portion 26 with respect to the actuating lever 16 to preclude pivotal rotation.

A magnifying lens 30 is coupled with respect to the lower portion 26 of the telescopic handle 20 disposed above the nail clipper 12. The magnifying lens 30 has a bifurcated outer end portion 32 slidably receiving the lower portion 26 of the telescopic handle 20 therein. A locking knob 34 extends through the bifurcated outer end portion 32 for selectively locking the magnifying lens 30 with respect to the lower portion 26 to preclude sliding of the lens 30.

In use, a user simply places their toe onto the triangular base 18 and positions their nail in the nail clipper 12. With the use of the hand, the user would press down on the telescopic handle 20 which will pressure the actuating lever 16 of the nail clipper 12 thereby cutting the nail. With the magnifying lens 30 positioned above the nail clipper 12, the user is better able to visualize the toe nail to be clipped. The user can adjust the magnifying lens 30 up or down to focus the lens 30 on the toenail being clipped. Additionally, the user can adjust the angle of the telescopic handle 20 with respect to the nail clipper 12 simply by loosening the locking knob 28.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A long handle toenail clipper for allowing a person to cut their toenails without needing to bend over comprising, in combination:

a conventional nail clipper having a cutting portion and an actuating lever;

a triangular base positioned below and secured to a lower segment of the cutting portion, the triangular base orienting the nail clipper with a forward end of the nail clipper disposed below a rearward end of the nail clipper;

a telescopic handle coupled to the actuating lever of the nail clipper, the telescopic handle having an upper portion, an intermediate portion and a lower portion, the lower portion pivotally coupled with the actuating lever of the nail clipper, a locking knob extending through the lower portion and the actuating lever for selectively locking the lower portion with respect to the actuating lever to preclude pivotal rotation; and a magnifying lens coupled with respect to the lower portion of the telescopic handle disposed above the nail clipper, the magnifying lens having a bifurcated outer end portion slidably receiving the lower portion of the telescopic handle therein, a locking knob extending through the bifurcated outer end portion for selectively locking the magnifying lens with respect to the lower portion to preclude sliding of the lens.

2. A long handle toenail clipper for allowing a person to cut their toenails without needing to bend over comprising, in combination:

a conventional nail clipper having a cutting portion and an actuating lever;

a triangular base positioned below and secured to a lower segment of the cutting portion, the triangular base orienting the nail clipper with a forward end of the nail clipper disposed below a rearward end of the nail clipper; and a telescopic handle coupled to the actuating lever of the nail clipper.

3. The long handle toenail clipper as set forth in claim 2 wherein the telescopic handle has an upper portion, an intermediate portion and a lower portion, the lower portion being pivotally coupled with the actuating lever of the nail clipper.

4. The long handle toenail clipper as set forth in claim 3 and further including a locking knob extending through the lower portion and the actuating lever for selectively locking the lower portion with respect to the actuating lever to preclude pivotal rotation.

5. The long handle toenail clipper as set forth in claim 2 and further including a magnifying lens coupled with respect to the telescopic handle disposed above the nail clipper.

6. The long handle toenail clipper as set forth in claim 5 wherein the magnifying lens has a bifurcated outer end portion slidably receiving a lower portion of the telescopic handle therein.

7. The long handle toenail clipper as set forth in claim 6 and further including a locking knob extending through the bifurcated outer end portion for selectively locking the magnifying lens with respect to the lower portion to preclude sliding of the lens.

\* \* \* \* \*